(12) United States Patent
Yokogawa et al.

(10) Patent No.: US 6,410,222 B1
(45) Date of Patent: Jun. 25, 2002

(54) IN OVO VACCINATION OF MAREK'S DISEASE TYPE I VIRUS

(75) Inventors: Kenji Yokogawa; Masashi Sakaguchi; Eiji Tokunaga, all of Kumamoto (JP)

(73) Assignee: Juridical Foundation The Chemosero-Therapeutic Research Institute, Kumamoto-ken (JP)

( * ) Notice: Subject to any disclaimer, the term of this patent is extended or adjusted under 35 U.S.C. 154(b) by 0 days.

(21) Appl. No.: 09/622,093

(22) PCT Filed: Feb. 8, 1999

(86) PCT No.: PCT/JP99/06866

§ 371 (c)(1),
(2), (4) Date: Aug. 11, 2000

(87) PCT Pub. No.: WO00/35476

PCT Pub. Date: Jun. 22, 2000

(30) Foreign Application Priority Data

Dec. 14, 1998 (JP) .................................... 10-354017

(51) Int. Cl.$^7$ .................. C12Q 1/70; A61K 39/245
(52) U.S. Cl. .................. 435/5; 424/229.1; 424/204.1; 424/184.1
(58) Field of Search .................. 424/229.1, 184.1, 424/204.1; 435/5

(56) References Cited

U.S. PATENT DOCUMENTS

| 5,558,867 A | 9/1996 | Sakaguchi et al. |
| 5,827,738 A | 10/1998 | Coussens et al. |
| 5,833,980 A | 11/1998 | Coussens et al. |
| 6,013,261 A | * 1/2000 | Sonoda et al. ............ 424/199.1 |

FOREIGN PATENT DOCUMENTS

| EP | A1650733 | 5/1995 |
| EP | 0748867 | 12/1996 |
| EP | A1774513 | 5/1997 |
| WO | A1-9104750 | 4/1991 |
| WO | A1-9314629 | 8/1993 |
| WO | 96/38565 | * 5/1996 |
| WO | 9640233 | 12/1996 |

OTHER PUBLICATIONS

J. M. Sharma et al., *Am. J. Vet. Res.*, vol. 45, pp. 1619–1623 (1984).
J. M. Sharma et al., *Avian Diseases*, vol. 27, No. 2, pp. 453–463 (1983).
P. A. Johnston et al., *Poultry Science*, vol. 76, pp. 165–178 (1997).
J. M. Sharma et al., *Avian Diseases*, vol. 26, No. 1, pp. 134–148 (1982).
J. M. Sharma et al., *Avian Diseases*, vol. 26, No. 4, pp. 860–870 (1983).
S. K. Reddy et al., *Vaccine*, vol. 14, No. 6, pp. 469–477 (1996).
G. Sarma et al., *Avian Diseases*, vol. 39, pp. 211–217 (1995).
J. M. Sharma, *Avian Diseases*, vol. 31, pp. 570–576 (1987).
R. L. Witter, *Avian Diseases*, vol. 41, pp. 149–163 (1997).
H. Stone et al., *Avian Diseases*, vol. 41, pp. 856–863 (1997).
Taniguchi et al., 117th Japanese Society of Veterinary Science, excerpt, p. 198, 1994, Tokyo (with English translation thereof).
R. L Witter, *Avian Diseases*, vol. 31, pp. 752–765 (1987).
H. Ogura et al., *Acta Med Okayama*, vol. 41, No. 3, pp. 141–143 (1987).
K. Tsukamoto et al., *Virology*, vol. 257, pp. 352–362 (1999).
M. Sakaguchi et al., *Virology*, vol. 195, No. 1, pp. 140–148 (1993).
M. S. Parcells et al., *J. Virology*, vol. 68, No. 12, pp. 8239–8253 (1994).
K. A. Schat et al., *J. General Virology*, vol. 79, pp. 841–849 (1998).
B. W. Calnek et al., *Applied Microbiology*, vol. 20, No. 5, pp. 723–726 (1970).
B. R. Cho, *Avian Diseases*, vol. 22, No. 1, pp. 170–176 (1977).
K. Sonoda et al., *Current Research on Marek's Disease*, pp. 408–413 (1996).

* cited by examiner

*Primary Examiner*—Ali R. Salimi
(74) *Attorney, Agent, or Firm*—Birch, Stewart, Kolasch & Birch, LLP

(57) ABSTRACT

The preset invention provides a method for immunizing chickens which comprises inoculating into growing egg a composition comprising either cell-free attenuated viruses of Marek's disease type 1 or cells infected with attenuated viruses of Marek's disease type 1 capable of producing cell-free viruses. The present invention also provides a method for immunizing chickens which comprises inoculating into growing egg a mixed vaccine comprising said composition plus another vaccine from at least one microorganisms selected from the group consisting of viruses other than virus of Marek's disease type 1, bacteria and protozoan.

11 Claims, No Drawings

IN OVO VACCINATION OF MAREK'S DISEASE TYPE I VIRUS

This application is the national phase under 35 U.S.C. §371 of PCT International Application No. PCT/JP99/06866 which has an International filing date of Feb. 8, 1999, which designated the United States of America.

The present invention relates to a prophylaxis for chicken Marek's disease induced by Marek's disease type I virus (hereinafter also referred to as "MDV-1"). More specifically, the present invention relates to a method for immunizing chickens comprising inoculating into a growing chicken egg either a composition comprising cell-free attenuated live MDV-1 or a composition comprising cells infected with attenuated live MDV-1 capable of producing cell-free viruses. Furthermore, the present invention provides a method for efficiently immunizing chickens against plural diseases with recombinant MDV-1.

BACKGROUND OF THE INVENTION

Marek's disease is a chicken infectious disease characterized by infiltration or tumorous proliferation of lymphoids by MDV-1 associated with symptoms such as leg paralysis, formation of lymphoma in various organs of viscera, weight loss, anemia, diarrhea, etc. In the field, Marek's disease leads chicken to death or partial or total disposal in a poultry laboratory and hence results in much economic loss in poultry farmer.

For protection from Marek's disease, attenuated live vaccine has hitherto been used, i.e. MDV-1, MDV-2 or herpes virus of turkey (HVT, MDV-3) alone or in admixture has been subcutaneously inoculated into newborn chicken. In such a case, a dosage form of virus-infected cells was usually employed. However, it was reported that as to Marek's disease virus with extremely high pathogenicity such as very virulent strain or very virulent (+) as reported in recent years, MDV-2 or HVT exhibits poor effectiveness but only vaccine of MDV-1 can effectively be used (R. L. Witter, AVIAN DISEASE 41: 149–163, 1997).

Nowadays, a number of vaccines have been developed for various chicken infectious diseases. Prophylaxis of diseases by vaccination is a ruling measure for sanitation in the field of poultry irrespective of breeding chicken, laying hen or chicken for meat. On the other hand, labor cost due to scale-up of poultry or crammed schedule of frequent inoculation of vaccine is a burden to poultry farmer. For obviating this, development of more effective and efficient vaccination such as reduction in frequency of inoculation by mixing several vaccines (i.e. mixed vaccine) or improvement of vaccination has been attempted.

As one of efficient way of vaccinations, Sharma et al. reported vaccination into growing chicken egg ("in ovo" inoculation) (J. M. Sharma et al., AVIAN DISEASE 26(1): 134–149, 1982). That is, according to Sharma et al., chicken hatched from a growing chicken egg inoculated with HVT-infected cells and chicken inoculated with said HVT after hatching were attacked by Marek's disease virus (hereinafter also referred to as "MDV"), and as a result, it was found that the chicken from vaccinated growing egg exhibited more potent resistance against the attack as compared to the chicken vaccinated after hatching, demonstrating that in ovo inoculation can effectively be used for immunization.

Reddy et al. prepared a recombinant HVT (rHVT) wherein a fusion protein (F protein) gene of Newcastle disease virus (hereinafter also referred to as "NDV") and hemagglutinin-neuraminidase (HN) glycoprotein gene of NDV were incorporated into HVT genome (S. K. Reddy et al., Vaccine 14(6): 469–477, 1996). They inoculated cells infected with this virus into growing chicken egg on day 18. After hatching, the chicken was attacked by both NDV and MDV viruses to thereby demonstrate that the recombinant virus could effectively protect the chicken from the attack of both viruses. The effect of in ovo vaccination has also been estimated for an inactivated oil-emulsified vaccine of NDV and avian influenza virus (H. Stone, AVIAN DISEASE 41: 856–863, 1997) or for live Eimeria sporozoite vaccine (Evans et al., WO 96/40233).

Chicken immunization at the stage of growing egg as described above, called "in ovo vaccination", can be expected to eliminate or reduce labor and cost and hence an automated device for inoculation into chicken egg becomes prevailing.

However, Sharma et al. reported that MDV-1-infected cells were inoculated into growing chicken egg and growth of said virus in chicken embryo tissue was investigated and, as a result, no viral growth was observed (J. M. Sharma et al., AVIAN DISEASES 31: 570–576, 1987). They also reported that chicken hatched from said growing egg was not protected from the attack of virulent MDV strain. This result suggests that in ovo vaccination against Marek's disease with MDV-1 is not so easy. Accordingly, it is the present situation that a univalent or mixed vaccine of HVT or MDV-2 SB-1 strain has alternatively been used as in place of MDV-1, a causing virus of Marek's disease.

On the other hand, there is a report of attempting to inoculate MDV-1, having been regarded as being ineffective for in ovo vaccination, into growing chicken egg (Taniguchi et al., 117th Japan Veterinary Science Association excerpt, p.198, 1994, Tokyo). In this case, if inoculation is made directly to fetus, the virus efficiently grew and successful immunization results. However, indeed, failure in direct inoculation to fetus frequently occurs. In spite of such circumstances, field application has been conducted because even if some individuals failed to be immunized, contact infection occurring about two weeks after MDV-1 inoculation would impart immunization to those individuals that failed to be immunized.

However, if non-immunized chicken is exposed to virulent MDV strain in the field after hatching and prior to infection with said MDV-1 vaccine by contact infection, then said chicken cannot be protected from Marek's disease and hence considerable economic loss will results. Thus, for thorough protection from Marek's disease, it is most important whether or not immunization is established within a week just after hatching. Accordingly, if possible, it is desirable to surely infect fetus in the growing egg with vaccine virus.

There is also a care that direct inoculation of needle into fetus might possibly damage the fetus badly in some cases.

Under the circumstances, there is a need to develop a more effective MDV-1 vaccine for Marek's disease that is applicable for in ovo vaccination.

DISCLOSURE OF THE INVENTION

The present inventors thoroughly investigated in order to develop a more effective MDV-1 vaccine for Marek's disease that is applicable for in ovo vaccination. As a result, it was found that a cell-free viral solution prepared from a solution of ruptured cells infected with either attenuated MDV-1 or recombinant MDV-1 was inoculated into growing egg to thereby exhibit viral growth. It was also found that antibodies to MDV-1 and to other viral antigens incorporated into MDV-1 were induced in serum of chicken that hatched from said virus-inoculated growing egg. As such, the present inventors have completed the present invention.

That is, an object of the present invention is to provide a method for immunizing chickens which comprises inoculating into growing egg a composition comprising either cell-free attenuated live MDV-1 or cells infected with attenuated live MDV-1 capable of secreting cell-free attenuated live MDV-1 out of the cells. The present invention also provides a method for efficiently immunizing chickens against plural diseases by using a recombinant MDV-1 in the above method for immunization.

Another object of the present invention is to provide a method for immunizing chickens which comprises inoculating into growing egg a mixed vaccine comprising the above cell-free MDV-1 plus another vaccine derived from at least one microorganisms selected from the group consisting of viruses other than MDV-1, bacteria and protozoan.

The method of the present invention is characterized by a composition comprising cell-free attenuated live MDV-1, a process for preparing the same and in ovo vaccination of said composition.

BEST MODE FOR CARRYING OUT THE INVENTION

The term "cell-free virus(es)" as used herein means viruses that are present in the state of being free from cells.

For preparing a composition comprising cell-free attenuated live MDV-1, attenuated MDV-1 viruses are infected to host cells and grown therein. The virus-infected cells are then collected by centrifugation at a low speed. After addition of a buffer supplemented with an appropriate amount of sugars, the cells are ruptured by sonication or freezing-thawing or by physically rupturing the cells. MDV-1 viruses are then extracted from the obtained solution of the ruptured cells and purified. For the purpose of the present invention, centrifugation at a low speed is carried out at 1,000 to 3,000 rpm for 3 to 10 minutes using KUBOTA, KN-30F or another centrifuging machine with equivalent turning radius. Alternatively, the obtained solution of ruptured cells may directly be used as it stands without any treatment.

Attenuated MDV-1 includes CVI-988 strain, 61-554 strain (Sakaguchi et al., Japanese Patent Publication No. 6-22757), Md11/75C (R. L. Witter, AVIAN DISEASE 31: 752–765, 1987) and the like as well as recombinant viruses derived therefrom.

The composition of the present invention may also be prepared by using attenuated MDV-1-infected cells capable of secreting cell-free viruses out of the cells. Such attenuated MDV-1-infected cells capable of secreting cell-free viruses out of the cells may be prepared by repeatedly culturing and growing cell-free attenuated MDV-1 occurring in a trace amount in supernatant of said virus-infected cells as described in more detail in Sakaguchi et al., Japanese Patent Publication No. 6-22757.

As a host cell for viral infection, any culture cell may be used as far as attenuated MDV-1 can grow therein and it does not produce contaminate viruses. Preferably, avian-derived culture cells are used. Chicken embryo fibroblast cells (CEF cells), duck embryo fibroblast cells, chicken embryo-derived cell strain CHCC-OU2 (Ogura, H. et al., Acta Med Okayama 41(3): 141–143, 1987, and Coussens et al., Japanese Patent Publication No. 9-173059), quail-derived cell strain QT-35 (Spijkers et al., Japanese Patent Publication No. 9-98778) and the like are used with chicken embryo fibroblast cells (CEF cells) being preferred.

A culture medium for culturing host cells includes a medium commonly used for tissue culture such as M199-earle base (Nissui), Eagle MEM (E-MEM) (Nissui), Dulbecco MEM (D-MEM) (Nissui), SC-UCM102 (Nissui), UP-SFM (GIBCO BRL), EX-CELL302 (Nichirei), EX-CELL293-S (Nichirei), TFBM-01 (Nichirei), ASF104, etc. These culture media are used with supplement of amino acids, salts, anti-fungal or anti-bacterial agent, animal serum and the like. They may optionally be used as a serum-free medium by not supplementing serum.

Cells or virus-infected cells are cultured under normal conditions. That is, culture temperature and period may appropriately be adjusted depending on various factors such as types of cells, inoculation amount of viruses and scale and process of culture or a combination thereof, culture temperature may range from 35° C. to 41° C., preferably from 37° C. to 38° C. and culture period may range from 2 to 7 days, preferably from 3 to 4 days.

The thus prepared composition of the present invention is inoculated into growing chicken egg. The term "growing chicken egg" as used herein means a fertilized egg that is incubated and in the progress until 21 days after fertilization when chicken is hatched. Vaccination for Marek's disease may be carried out after incubation for 17 to 19 days.

The composition of the present invention may be inoculated into growing chicken egg by, for example, injecting an inoculation needle (e.g. 24G1·¼ needle) into growing chicken egg of 18 days old at an air chamber (i.e. at an obtuse-angled site of egg) to introduce viral solution.

In accordance with the composition of the present invention comprising either cell-free attenuated MDV-1 or attenuated MDV-1-infected cells capable of producing cell-free viruses, attenuated MDV-1 can efficiently infect in the growing egg and induce immunization for Marek's disease.

The composition of the present invention may also be used for in ovo vaccination as a mixed vaccine in combination with at least one vaccine selected from the group consisting of vaccines to other viruses such as e.g. avian infectious bronchitis virus, avian infectious bursal disease virus, avian encephalomyelitis virus, egg drop syndrome virus, influenza virus, reovirus, adenovirus, hydropericardium syndrome virus, etc.; bacteria such as e.g. *Haemophilus paragallinarum, Salmonella typhimurium, S. enteritidis, S. pullorl, S. gallinarum, S. choleraesuis, E. coli,* Clostridium spp., Campylobacter spp., Mycoplasma spp., enterococcus, etc.; and protozoan such as e.g. *Leucocytozoon caulleryi, Eimeria tenella, E. maxima, E. acervulina, E. brunetti, E. necatrix,* chicken malaria, etc.

Infection-protecting antigen expressed by the recombinant Marek's disease virus used in the present invention includes, in addition to F protein of Newcastle disease virus exemplified above, HN protein of Newcastle disease virus, core protein, capsid protein or glycoprotein of various viruses (e.g. spike protein or nucleocapsid protein of avian infectious bronchitis virus, VP2 of avian infectious bursal disease virus (IBDV), capsid protein of avian encephalomyelitis, capsid protein of egg drop syndrome virus, VP1+VP2 of avian anemia virus, glycoprotein B of avian infectious laryngotracheitis, membrane protein or gag of avian leukemia virus or reticuloendotheliosis, glycoprotein of rhinotracheitis of turkeys virus, HA protein of avian pox virus, HA of influenza virus, capsid protein of avian reovirus, capsid protein of avian adenovirus, etc.), cilia, flagella, toxins, hemolysins, membrane proteins such as porin, peptides with antigenicity of O-antigen of bacteria (e.g. *Haemophilus paragarinarum, Salmonella*

*choleraesuis, E. coli,* Campylobacter, Clostridium, Mycoplasma, enterococcus, etc.), and proteins or glycoproteins from protozoan (e.g. *Leucocytozoon caulleryi, Eimeria tenella, E. maxima, E. acervulina, E. brunetti, E. necatrix,* avian malaria), and the like.

Such recombinant Marek's disease virus can be prepared using an ordinary process for preparing a recombinant virus well known in the art.

Other than ND, antigens that were actually incorporated into a recombinant MDV-1 and reported to be immunogenic in chicken includes IBDV-VP2 antigen as reported by Tsukamoto et al., Virology 257: 352–362, 1999. A plural of recombinant viruses incorporating marker gene, lacZ, were also reported (Sakaguchi et al., Virology 195: 140–148, 1993; Percells et al., J. Virology 68: 8239–8253, 1994; Schat et al., J. gen. Virology 70: 841–849, 1998).

The present invention is explained in more detail by means of the following Examples, but should not be construed to be limited thereto.

EXAMPLE

EXAMPLE 1

In Ovo Vaccination of MDV-1

(1) Preparation of Materials for Inoculation of Growing Chicken egg

About $1\times10^8$ CEF: cells and about $1\times10^6$ PFU of MDV-1 Rispens strain were suspended in E-MEM medium (40 ml) supplemented with 5% fetal bovine serum (FBS). The suspension was placed in a 175 $cm^2$ culture flask and incubated at 37° C. for 4 days. When 80% or more cytopathic effect (CPE) was observed, virus-infected cells were collected in a usual manner employing 0.1% EDTA–0.125% trypsin (DIFCO). The collected cells were suspended in 40 ml of E-MEM medium. From this suspension, materials for inoculation into growing chicken egg were prepared by the following two processes:

(a) A solution of Virus-infected Cells

The above suspension (1 ml) was serially diluted 10-fold with E-MEM to prepare a solution of virus-infected cells.

(b) A Solution of Cell-free Viruses

The remaining suspension (39 ml) was centrifuged at a low speed at 1,500 rpm for 5 minutes. After removing supernatant by suction, the cells were suspended by adding 2 ml of SPGA-SBT solution (prepared in accordance with B. W. Calnek et al., Appl. Microbiol. (20): 723–726, 1970; B. R. Cho, Avian Dis. 22 (1): 170–176, 1977; 0.218 M sucrose, 0.0038 M potassium dihydrogenphosphate, 0.0072 M dipotassium hydrogenphosphate, 0.0049 M sodium glutamate, 1% bovine serum albumin, 10% sorbitol). The suspension was sonicated with TOMY SEICO Co., LTD, Handy sonic UR-20P, Power cont. 4 for 1 minute and then centrifuged at a low speed at 2,500 rpm for 5 minutes. The obtained supernatant was serially diluted 10-fold to prepare a solution of cell-free viruses.

Viruses in the inoculation materials were counted as follows: CEF cells previously cultured were collected with EDTA-trypsin and centrifuged at 1,500 rpm for 5 minutes. The obtained cellular sediment was again suspended in 5%-FBS at a concentration of $6\times10^5$ cells/ml (hereinafter referred to as "CEF2nd").

The CEF2nd cells, ($9\times10^6$ cells/15 ml in a 10 cm Petri dish) were cultured for 4 hours and inoculated with 1 ml of a vaccine solution of each dilution by tilting every 20 minutes for 1 hour. The cells were then added with E-MEM medium (5 ml) and incubated in $CO_2$, incubator at 37° C. overnight. The next day, E-MEM supplemented with 2% methyl cellulose (Sigma) and 1% FCS was overlaid, the cells were incubated in $CO_2$ incubator at 37° C. for 10 days and the number of plaques appeared was counted.

(2) Inoculation into Growing Chicken Egg

Each group consisted of six growing chicken eggs of 18 days old (SPF manufactured by Juridical Foundation The Chemo-Sero-Therapeutic Research Institute). Each 0.1 ml of the solution of virus-infected cells serially diluted 10-fold or of the solution of cell-free viruses was inoculated into the egg by injecting 24G1·¼ inoculating needle (Nipro) at an air chamber (an obtuse angled site) of the egg with about 2.5 cm depth. The eggs were incubated at 37° C. for 3 days. A week after hatching, 1 ml of blood was drawn from the heart with a heparinized 5 ml disposable syringe (Nipro) and 21G 1 inch needle (Nipro). A fraction of mononuclear cells was separated from said blood using Ficoll Paque Plus (Pharmacia) in. accordance with a manufacture's instruction. A total of this fraction was inoculated into CEF2nd cells ($9\times10^6$ cells/15 ml, in Petri dish of 10 cm diameter) previously cultured for 4 hours. Ten days later, plaques of Marek's disease viruses appeared were counted. Recovery rates of viruses in the group of inoculation with the solution of virus-infected cells and in the group of inoculation with the solution of cell-free viruses are shown in Tables 1 and 2, respectively. Among hatched chicken, blood was drawn from each 5 chicken in the groups to conduct viral recovery.

TABLE 1

| Inoculated amount per chicken (PFU) | Rate of viral infection (Positive No./Total No.) |
| --- | --- |
| 1280 | 4/5 |
| 128 | 2/5 |
| 12.8 | 0/5 |
| 1.28 | 0/5 |

TABLE 2

| Inoculated amount per chicken (PFU) | Rate of viral infection (Positive No./Total No.) |
| --- | --- |
| 540 | 5/5 |
| 54 | 5/5 |
| 5.4 | 5/5 |
| 0.54 | NT |

As apparent from Tables 1 and 2, viruses were recovered from merely less than the half of the individuals among chicken from eggs inoculated with 128 PFU in the group of inoculation with the solution of virus-infected cells. On the contrary, in the group 2 inoculated with the solution of cell-free viruses, viruses were recovered from all the five chicken even in the group inoculated with as low as 5.4 PFU. This demonstrates that MDV-1 viruses indeed propagate in case of the solution of cell-free viruses and hence the solution of cell-free viruses can effectively be used.

EXAMPLE 2

In Ovo Vaccination of Recombinant MDV-1

(1) Preparation of Materials for Inoculation of Growing Chicken Egg

About $1\times10^8$ CEF cells and about $1\times10^6$ PFU of recombinant virus rMDV1 US10P(F) strain wherein a gene for Newcastle disease virus F (NDV-F) protein was incorporated (Sonoda et al., Current research on Marek's disease, p.408, 1996) were suspended in E-MEM medium (40 ml)

supplemented with 5% fetal bovine serum (FBS). The suspension was placed in a 175 cm² culture flask and incubated at 37° C. for 4 days. When 80% or more cytopathic effect (CPE) was observed, virus-infected cells were collected in a usual manner employing 0.1% EDTA–0.125% trypsin (DIFCO). The collected cells were suspended in 10 ml of E-MEM medium. From this suspension, materials for inoculation into growing chicken egg were prepared by the following processes:

Preparation of a Solution of Cell-free Viruses

As described in Example 1 (1), the suspension (40 ml) was centrifuged at a low speed at 1,500 rpm for 5 minutes. After removing supernatant by suction, the cells were suspended by adding 2 ml of SPGA-SBT solution. The suspension was sonicated for 1 minute and then centrifuged at a low speed at 2,500 rpm for 5 minutes. The obtained supernatant was serially diluted 10-fold to prepare a solution of cell-free viruses.

As described in Example 1(1), viruses in the inoculation materials were counted as follows: i.e. the CEF2nd cells ($9 \times 10^6$ cells/15 ml in a Petri dish of 10 cm diameter) were prepared as described in Example 1 (1) and previously cultured for 4 hours. The cells were inoculated with 1 ml of a vaccine solution of each dilution by tilting every 20 minutes for 1 hour. The cells were then added with E-MEM medium (5 ml) and incubated in $CO_2$ incubator at 37° C. overnight. The next day, E-MEM supplemented with 2% methyl cellulose (Sigma) and 1% FCS was overlaid, the cells were incubated in $CO_2$ incubator at 37° C. for 10 days and the number of plaques appeared was counted.

(2) Inoculation into Growing Chicken Egg

Each group consisted of five growing chicken eggs of 18 days old (SPF manufactured by Juridical Foundation The Chemo-Sero-Therapeutic Research Institute). Each 0.1 ml of the solution of virus-infected cells serially diluted 10-fold or of the solution of cell-free viruses was inoculated into the egg by injecting 24G1·¼ inoculating needle (Nipro) at an air chamber (an obtuse angled site) of the egg with about 2.5 cm depth. The eggs were incubated at 37° C. for 3 days. A week after hatching, 1 ml of blood was drawn from the heart with a heparinized 5 ml disposable syringe (Nipro) and 21G 1 inch needle (Nipro). A fraction of mononuclear cells was separated from said blood using Ficoll Paque Plus (Pharmacia) in accordance with a manufacture's instruction. A total of this fraction was inoculated into CEF2nd cells ($9 \times 10^6$ cells/15 ml, in Petri dish of 10 cm diameter) previously cultured for 4 hours. Ten days later, plaques of Marek's disease virus appeared were counted.

TABLE 3

| Inoculated amount per chicken (PFU) | Rate of viral infection (Positive No./Total No.) | Average Viremia[1] |
|---|---|---|
| 320 | 5/5 | 3.27 |
| 32 | 5/5 | 1.82 |
| 3.2 | 3/5 | 1.61 |
| 0.32 | 0/5 | NT |

[1]Viral amount per $1 \times 10^6$ mononuclear cells

As apparent from Table 3, viruses were recovered from all the five chicken even in the group inoculated with as low as 32 PFU. Thus, effectiveness of the solution of cell-free viruses was confirmed in case of recombinant MDV-1 virus.

(3) Antibody Test

Growing chicken eggs were inoculated as described above except that each group consisted of six growing chicken eggs of 18 days old (SPF manufactured by Juridical Foundation The Chemo-Serb-Therapeutic Research Institute). When chicken from the growing eggs became 8 weeks old, blood was drawn and an antibody to NDV-F protein was determined.

The antibody was detected by ELISA with NDV-F expressing cells as an antigen. Detail of this procedure is described in Sakaguchi M. et al., Vaccine, 1996 June, 14(8): 747–52. Rates of NDV-F antibody positive individuals in the group of inoculation with the solution of virus-infected cells and in the group of inoculation with the solution of cell-free viruses are shown in Tables 4 and 5, respectively.

TABLE 4

| Inoculated amount per chicken (PFU) | Rate of NDV-F Ab positive individuals (Positive No./Total No.) |
|---|---|
| 84 | 2/6 |
| 8.4 | 0/6 |

TABLE 5

| Inoculated amount per chicken (PFU) | Rate of NDV-F Ab positive individuals (Positive No./Total No.) |
|---|---|
| 70 | 5/5 |
| 7 | 4/6 |
| 0.7 | 2/6 |
| No inoculation | 0/6 |

As shown in Table 5, all the chickens were positive for the antibody in the group of chickens from the eggs inoculated with 70 PFU cell-free viruses. In the group of chickens from the eggs inoculated with 7 PFU cell-free viruses, four among six chickens were positive. On the contrary, in the group of chickens inoculated with the solution of virus-infected cells, only two among six chickens were found to be positive when 84 PFU was inoculated. Thus, the cell-free virus inoculated group showed a higher positive conversion even with a lower amount of viruses by 10-fold than the virus-infected cells group, demonstrating usefulness of the cell-free viruses for immunization of growing egg in view of antibody response.

INDUSTRIAL APPLICABILITY

In accordance with the present invention, there are provided MDV-1 live vaccine for prophylaxis of chicken Marek's disease and a method for immunization by in ovo inoculation using said live vaccine. The method of the present invention allows for protection from Marek's disease virus infection more efficiently and effectively as compared to the conventional methods. Furthermore, the method of the present invention also allows for immunization for foreign gene products simultaneously expressed by MDV-1 in a laborsaving manner.

All the disclosures of all publications (including patents, patent applications, periodical publications, laboratory manuals, books and other publications) recited herein are incorporated herein for reference.

What is claimed is:

1. A method for immunizing chickens which comprises inoculating into a growing egg a composition comprising either cell-free attenuated live viruses of Marek's disease type 1 or cells infected with attenuated live viruses of Marek's disease type 1 capable of producing cell-free viruses.

2. The method of claim 1 wherein said attenuated viruses of Marek's disease type 1 are a recombinant virus of Marek's disease type 1.

3. The method of claim 2 wherein genes incorporated into said recombinant virus of Marek's disease type 1 code for antigens from viruses other than Marek's disease type 1 virus, bacteria or protozoa.

4. The method of claim 3 wherein said antigens are selected from the group consisting of F protein of Newcastle disease virus, HN protein of Newcastle disease virus, spike protein of avian infectious bronchitis virus, core protein of avian infectious bronchitis virus, VP2 of avian infectious bursal disease, virus (IBDV), capsid protein of avian encephalomyelitis, capsid protein of egg drop syndrome virus, VP1+VP2 of avian anemia virus, glycoprotein B of avian infectious laryngotracheitis, membrane protein of avian leukemia virus of reticuloendotheliosis, gag of avian leukemia virus of reticuloendotheliosis, glycoprotein of rhinotracheitis of turkeys virus, HA protein of avian pox virus, HA of influenza virus, capsid protein of avian reovirus, capsid protein of avian adenovirus, cilia, flagella, toxins, hemolysins, membrane proteins, peptides with antigenicity of O-antigen and proteins of glycoproteins from protozoa.

5. A method for immunizing chickens which comprises inoculating into a growing egg a mixed vaccine comprising either cell-free attenuated viruses of Marek's disease type I or cells infected with attenuated viruses of Marek's disease type 1 capable of producing cell-free viruses plus another vaccine derived from at least one microorganism selected from the group consisting of viruses other than MDV-1, bacteria and protozoa.

6. The method of claim 5 wherein said microorganisms are selected from the group consisting of avian infectious bronchitis virus, avian infectious bursal disease virus, avian encephalomyelitis virus, egg drop syndrome virus, influenza virus, reovirus, adenovirus, hydropericardium syndrome virus, bacteria and protozoan.

7. The method of claim 5 or 6 wherein said microorganisms are not inactivated.

8. A method for immunizing chickens which comprises inoculating into a growing egg a composition comprising cell-free attenuated live viruses of Marek's disease type 1.

9. The method of claim 8 wherein said attenuated viruses of Marek's disease type 1 are a recombinant virus of Marek's disease type 1.

10. The method of claim 9 wherein genes incorporated into said recombinant virus of Marek's disease type 1 code for antigens from viruses other than Marek's disease type 1 virus, bacteria or protozoa.

11. The method of claim 10 wherein said antigens are selected from the group consisting of F protein of Newcastle disease virus, HN protein of Newcastle disease virus, spike protein of avian infectious bronchitis virus, core protein of avian infectious bronchitis virus, VP2 of avian infectious bursal disease virus (IBDV), capsid protein of avian encephalomyelitis, capsid protein of egg drop syndrome virus, VP1+VP2 of avian anemia virus, glycoprotein B of avian infectious laryngotracheitis, membrane protein of avian leukemia virus of reticuloendotheliosis, gag of avian leukemia virus of reticuloendotheliosis, glycoprotein of rhinotracheitis of turkeys virus, HA protein of avian pox virus, HA of influenza virus, capsid protein of avian reovirus, capsid protein of avian adenovirus, cilia, flagella, toxins, hemolysins, membrane proteins, peptides with antigenicity of O-antigen and proteins of glycoproteins from protozoa.

* * * * *

UNITED STATES PATENT AND TRADEMARK OFFICE
CERTIFICATE OF CORRECTION

PATENT NO. : 6,410,222 B1
DATED : June 25, 2002
INVENTOR(S) : Kenji Yokogawa et al.

It is certified that error appears in the above-identified patent and that said Letters Patent is hereby corrected as shown below:

<u>Title page,</u>
Item [22], PCT Filed:, please correct the PCT filing date from "Feb. 8, 1999" to -- Dec. 8, 1999 --.

Signed and Sealed this

First Day of July, 2003

JAMES E. ROGAN
*Director of the United States Patent and Trademark Office*